(12) United States Patent
Sierra et al.

(10) Patent No.: US 6,749,602 B2
(45) Date of Patent: Jun. 15, 2004

(54) METHOD AND APPARATUS FOR THE DOUBLE OUTPUT TREATMENT OF PIGMENTED LESIONS AND TATTOOS

(75) Inventors: Rafael Armando Sierra, Palmer, MA (US); Addison C. Zukeran, Lowell, MA (US); Eric Calvin Koschmann, Hudson, NH (US)

(73) Assignee: Cynosure, Inc., Chelmsford, MA (US)

( * ) Notice: Subject to any disclaimer, the term of this patent is extended or adjusted under 35 U.S.C. 154(b) by 72 days.

(21) Appl. No.: 10/090,694

(22) Filed: Mar. 4, 2002

(65) Prior Publication Data

US 2002/0123782 A1 Sep. 5, 2002

Related U.S. Application Data

(60) Provisional application No. 60/273,165, filed on Mar. 3, 2001.

(51) Int. Cl.$^7$ ................................................. A61B 18/20
(52) U.S. Cl. .............................. 606/9; 128/898; 606/11
(58) Field of Search ............................ 606/2, 3, 9–13; 128/898

(56) References Cited

U.S. PATENT DOCUMENTS

| | | | | |
|---|---|---|---|---|
| 4,630,275 A | * | 12/1986 | Rapoport | ..................... 372/13 |
| 5,217,455 A | | 6/1993 | Tan | |
| 5,290,273 A | | 3/1994 | Tan | |
| 5,530,582 A | * | 6/1996 | Clark | ..................... 359/333 |
| 5,586,981 A | * | 12/1996 | Hu | ..................... 606/9 |
| 5,963,575 A | * | 10/1999 | Muller et al. | ................. 372/92 |
| 6,015,404 A | * | 1/2000 | Altshuler et al. | ............... 606/9 |
| 6,554,825 B1 | * | 4/2003 | Murray et al. | ................ 606/11 |

* cited by examiner

*Primary Examiner*—Lee Cohen
*Assistant Examiner*—Henry M Johnson
(74) *Attorney, Agent, or Firm*—Don Halgren

(57) ABSTRACT

A method and apparatus for treating lesions and tattoos sites. The method includes the steps of irradiating said lesion by a first single pulse Q-Switched laser beam directed onto the site; and again irradiating the lesion by a second single pulse Q-Switched laser beam directed onto the same lesion site within a time interval of less than about 100 μs.

15 Claims, 2 Drawing Sheets

METHOD AND APPARATUS FOR THE DOUBLE OUTPUT TREATMENT OF PIGMENTED LESIONS AND TATTOOS

This application claims the benefit of Provisional Application No. 60/273,165 filed Mar. 3, 2001.

BACKGROUND OF THE INVENTION

1. Field of the Invention

This invention relates to laser apparatus and more particularly to laser apparatus for the treatment and/or removal of lesions and tattoos.

2. Prior Art

Pigmented lesions are common conditions of the skin of humans. Those lesions may be dermal lesions and include nevus of ota, nevus of ito, or epidermal lesions, including solar lentigenes, and freckles, liver or age spots, and birth marks.

Pigmented lesions include tattoos. These may be human caused tattoos and traumatic tattoos which are the result of an accident or mishap such as a scrape or an abrasion or the like where some foreign material becomes embedded under the skin. In each case, the skin becomes pigmented and scarred. The tattoos are made by dyes or inks which are deposited into the skin by a needle to create coloration and patterns on the skin of an individual. Tattoos are usually created by a vibrating needle by which colored pigments are introduced into the skin, usually to the papillary layer of the dermis. Tattoos may be green, blue, brown, black, bluegreen, aqua and red, yellow or orange. At some point in the lives of individuals having such lesions or tattoos, a decision is made in the attempt to remove those same colorations from their skin. Treatment of such pigmented lesions in the field of dermatology often involves a short pulse Q-Switched laser. Absorption of the energy of a short pulse from a Q-Switched laser effects a rapid heating and high pressure in the target tissue which is exposed to the laser radiation, resulting in an efficient breakup of that tissue structure. The disrupted structure begins to clear up by the normal immunological response. The tattoo is such a structure which is treated by means of the short pulse Q-Switched laser. Such lasers may include the ruby laser, the Alexandrite laser and the Nd:YAG laser.

Q-Switched Alexandrite lasers are commonly limited to an output of about one joule/pulse. The fluence required to treat a tattoo effectively then limits the area that can be treated from a single pulse to the order of about 3 mm diameter. Larger output is possible by the use of amplifier stages or by the use of large volume laser rods. These methods are complex and expensive and have limited commercial appeal.

The prior art such as found in U.S. Pat. No. 5,217,455 and 5,290,273, both issued to Oon T. Tan disclose Q-switched Alexandrite laser arrangements for the treatment of tattoos. Such treatment utilizes a single pulse of laser radiation to a chosen site, with multiple treatments applied over a period of weeks and/or months.

It is an object of the present invention to provide a method and apparatus for the treatment for pigmented lesions and tattoos which is an improvement over the prior art.

It is a further object of the present invention to provide a Q-Switched laser having improved output pulses and output energy for the treatment of lesions and tattoos than does the prior art.

It is still a further object of the present invention, to provide a Q-Switched laser which permits larger spot sizes at high repetition rate for treatment for lesions and tattoos than does the prior art.

It is still yet a further object of the present invention to provide a Q-Switched laser which minimizes the overall treatment time necessary for lesions and tattoos.

It is still yet a further object of the present invention to provide a Q-Switched laser arrangement which will minimize the number of treatments necessary for lesions and tattoos.

BRIEF SUMMARY OF THE INVENTION

The present invention involves a laser arrangement for the treatment of pigmented lesions or tattoos. In a typical treatment of a pigmented lesion or tattoo, the area of the lesion is irradiated with the laser. The laser output is characterized by short pulses of high peak power often in excess of 10 M watt. Immediately following a laser pulse, the area irradiated undergoes blanching caused by vaporization of tissue in the neighborhood of the pigment. A second laser pulse delivered to this area after vaporization would experience a great deal of scattering, thus preventing the laser light from reaching the intended target and consequently not being very effective at providing any further breakup of the pigmented structure. The time frame for the tissue vaporization to occur is or the order of 100 $\mu$s. If a second Q-Switched pulse is delivered to the pigmented lesion within that time interval, it would not experience the large scattering and therefore that second laser pulse can be very effective in treating that lesion.

It is common in the treatment of tattoos to increase the laser fluence as the lesion clears. The increase is needed since as the tattoo clears, there is less pigment to absorb the laser energy and, increased fluence (energy per unit area provided by a laser beam at a target site) is needed to insure that sufficient energy is absorbed by the pigment. If two pulses are delivered to the tissue in a window of less than about 100 $\mu$s, then the amount of pigment available to absorb the laser will be the same for both pulses.

A typical flashlamp excited solid state laser such as an Alexandrite laser uses a gain medium typically in the shape of a cylindrical rod. A flashlamp provides radiation needed to excite the rod, and a reflective chamber is used to insure that the radiation from the lamp reaches the laser rod. The radiation from the flashlamp excites the gain medium. Spontaneous radiation is emitted from the excited gain medium. Some of this radiation is reflected back into the gain medium by a pair of carefully aligned mirrors that form a resonator. This radiation experiences amplification as it traverses the gain medium. One of the mirrors is partially transmitting thus allowing a useful output from the laser. Stable laser oscillation begins when the round trip gain experienced by the radiation exactly balances the round trip losses, including the amount of radiation that exits the laser as useful output.

If a large loss is introduced in the laser resonator, the gain needed to achieve laser oscillation will be very large. A large amount of energy can be deposited in the laser rod achieving a large gain without laser oscillation taking place. If the losses are removed very rapidly while the gain in the medium is very high, the resulting laser will be well above threshold. The radiation in the resonator will grow very rapidly and a giant, short pulse will be developed and a portion of the energy previously deposited in the rod will be its output. This process is called "Q-Switching".

The fraction of the energy stored in the rod that is extracted in a Q-Switched pulse depends on a number of factors including how much above threshold the laser is immediately after the losses are removed from the resonator, the energy resident in the rod at that time, and an inherent quantity of the gain medium commonly called the "saturation" fluence. This is the fluence that must be present in the resonator in order to extract a large fraction of the energy stored in the rod. The saturated fluence is the ratio of the emitted photon energy divided by the stimulated emission cross-section of the material. For the case of Alexandrite, the stimulated emission cross-section is very small, resulting in a large saturation fluence. As a result, in a common Alexandrite laser under flashlamp excitation, only a small fraction of the energy stored is extracted in the Q-Switch process. A significant fraction remains stored in the rod, If the resonator losses are restored, and the flashlamp excitation is extended past the time where the Q-Switch pulse was extracted, the stored energy in the rod will once again increase. Since a significant amount of energy is already present in the rod, the stored energy will reach a level equal to the level at which the first pulse was extracted with less energy from the flashlamp. That is, a second pulse whose energy is equal to that of the first may be extracted from the rod and will require less additional energy than the first one. The process may be continued for additional pulses.

To achieve efficient two pulse operation, the time between the two pulses should not exceed the radiative lifetime of the excited medium. For the case of Alexandrite, this time of the order of 100 μs. It follows then that a dual pulse Alexandrite laser can meet the requirements set forth for a dual pulse tattoo treatment.

There are many benefits to this type of operation. First, it is clear that the laser output will be twice that of a typical Q-Switched laser without the need for amplifiers or a large expensive laser rods. Because the peak power is not increased, the laser delivery optics are not stressed more than they are in a singe pulse case. This is particularly important when the laser delivery uses optical fibers. In many cases these fibers operate close to their damage point and doubling the output energy in a single pulse can otherwise seriously reduce their reliability.

The "pulse timing" of the present invention may, in further embodiments be utilized in a treatment with a catheter-based light generation (Alexandrite laser) application where similar limited-time constraints on the order of 1 millisecond or less (such as for example as low as 0.1 millisecond) are needed. Those applications may include the opening of occluded lumens, the breakup of objects within the body or in body lumens. Such examples may include the treatment of arthroscopic plaque, kidney stones or calculi or the like.

The present invention thus comprises a method of treating a lesion or tattoo site on tissue of a human patient in a lasing procedure by the steps of: irradiating the lesion by a first independent single pulse Q-Switched laser beam directed onto the site; and irradiating the lesion by a second independent single pulse Q-Switched laser beam directed onto the site within a time interval of less than about 100 μs after the first pulse.

The method may also include the steps of: irradiating the lesion again by a further single pulse Q-Switched laser beam directed onto the site within the time interval of less than about 100 μs. The first pulse and the second pulse may each have a range of pulse duration of about 50 nanoseconds to about 75 nanoseconds. The first pulse and the second pulse may each have preferably a pulse duration of about 60 nanoseconds. The Q-switched laser may be comprised of Alexandrite. The Alexandrite laser may have a wavelength of about 755 nm. The Alexandrite laser may have a maximum fluence of about 30 Joules/cm$^2$ at 2.4 mm. The Alexandrite laser may have a maximum fluence of about 20 Joules/cm$^2$ at 3.0 mm. The Alexandrite laser may have a maximum fluence of about 7 Joules/cm$^2$ at 5.0 mm.

The present invention may also comprise a flashlamp excited Alexandrite laser arrangement with a driven laser rod for the treatment of pigmented lesions and tattoos. The arrangement may include: a Q-Switch driver for effecting Q-Switching of the laser resonator to output single laser pulses onto a site to be treated wherein at least two single pulses are enabled to be applied to the site within a time window equivalent to about 100 μs. Each of the single laser pulses may preferably have a pulse duration in a range of about 50 nanoseconds to about 75 nanoseconds. Each of the single laser pulses may have a pulse duration of about 60 nanoseconds. The Alexandrite laser may have a wavelength of about 755 nm. The laser may have a maximum fluence of about 30 J/cm$^2$ at 2.4 mm. The laser may in another embodiment have a maximum fluence of about 20 J/cm$^2$ at 3.0 mm. The laser in a further embodiment have a maximum fluence of about 7 J/cm$^2$ at 5.0 mm.

BRIEF DESCRIPTION OF THE DRAWINGS

The objects and advantages of the present invention will become more apparent when viewed in conjunction with the following drawings in which.

DESCRIPTION OF THE PREFERRED EMBODIMENTS

Figure 1:
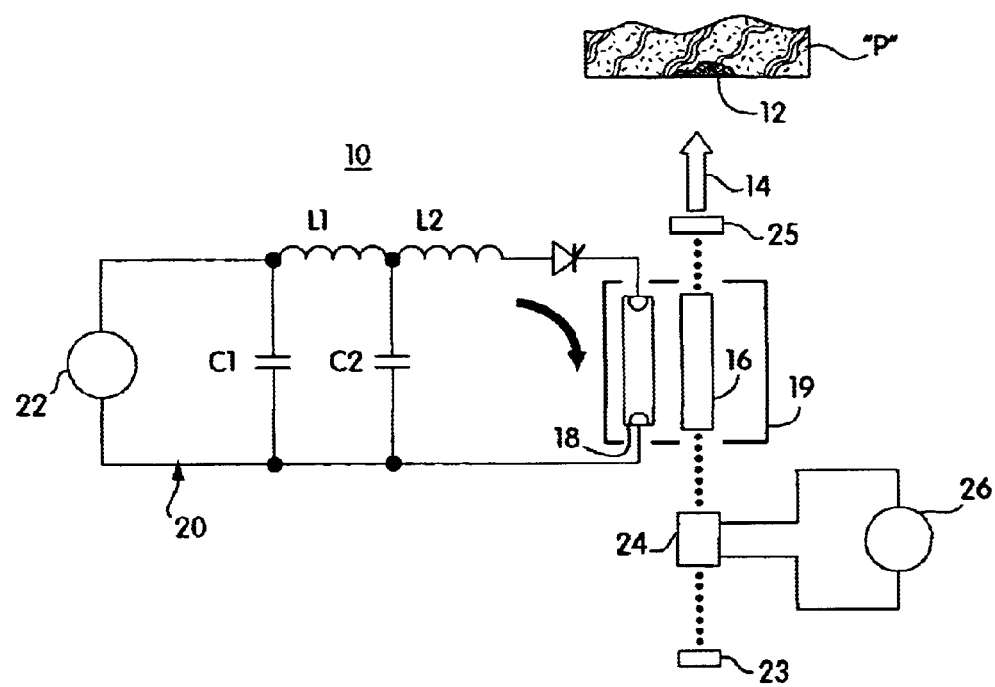
FIG. 1 is a schematic representation of a laser apparatus for the treatment of pigmented lesions and tattoos.

Referring now to the drawings in detail and particularly to FIG. 1, there is shown the present invention which comprises a laser arrangement 10 for the treatment of pigmented lesions or tattoos 12 on a mammalian patient "P". The laser arrangement 10 comprises a laser rod 16, of in a first preferred embodiment for example Alexandrite, excited by a flashlamp 18.

Further preferred embodiments of the laser rod 16 may be comprised of a Ruby laser or a laser rod comprised of Nd:YAG. The flashlamp 18 for these embodiments is powered by a proper circuit 20 including a high voltage power supply 22. The laser rod 16 has a 100% reflective mirror 23 at a rear end thereof, and a partial reflective mirror 25 at its output end as may be seen in FIG. 1. A Q-Switch 24, controlled by an interconnected Q-Switch driver 26 governs the pulse generation and output of the laser 10. In a typical treatment of a pigmented lesion or tattoo 12, the area of the lesion is irradiated with the laser beam 14. The laser output is characterized by a high peak power often in excess of 10 M watt. The preferred pulse duration (the time interval during which a laser beam strike's its target site, typically of nanosecond length) for the present invention may extend for a range of about 50 to 75 nanoseconds, and is preferably about 60 nanoseconds. Almost immediately following the laser pulse, the area irradiated undergoes blanching caused by vaporization of tissue in the neighborhood of the pigment. A second laser pulse delivered to this area of the lesion or tattoo 12 after tissue vaporization would experience a great deal of beam pulse scattering and not be very effective at providing any further breakup of the pigmented structure. The time frame for the vaporization to occur is or the order of about 100 μs. If a second Q-Switched pulse of about 60 nanosecond duration is delivered to the pigmented lesion within that critical time interval of about 100 μs from the first pulse, that second Q-switched pulse would not experience the large scattering and that second laser pulse would be very effective, as has been demonstrated clinically. The second pulse thus improves the effect and treatment realized in a single clinician visit.

It is common in the prior art treatment of tattoos to increase the laser fluence as the lesion clears. The increase is needed since as the tattoo clears, there is less pigment to absorb the laser energy and, increased fluence is needed to insure that sufficient energy is absorbed.

In the present invention however, at least two Alexandrite laser pulses, each pulse of about 60 nanosecond duration, are delivered to the tissue target site in a "time window" of less than about 100 μs, so that the amount of pigment available to absorb the laser will be the same for each pulse. That is, both pulses can be equally effective. Further embodiments contemplate a combination of multiple pulses which may become even more effective depending upon the number of pulses within that 100 μs "window".

Figure 2:
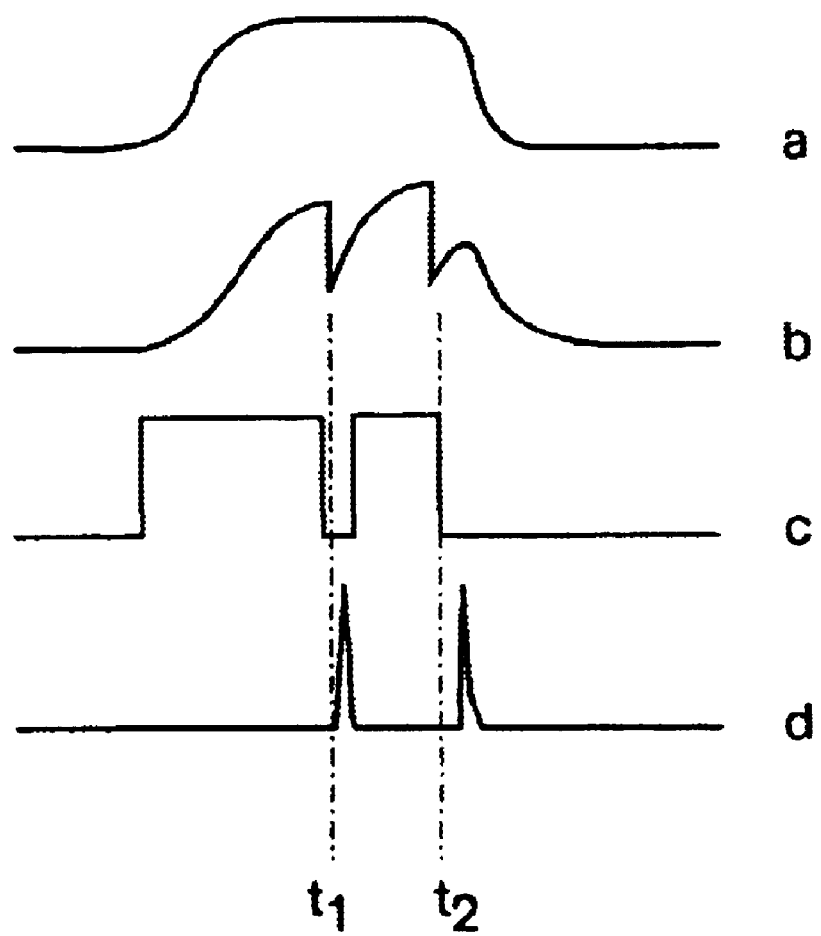
FIG. 2 discloses traces of pulses associated with the laser apparatus for treatment of pigmented lesions and tattoos.

As may be seen in FIG. 2, pulse traces are displayed for the laser treatment arrangement 10 shown in FIG. 1. Trace "a" represents the current pulse that drives the laser flashlamp 18. As indicated on trace "c", at the time the flashlamp 18 is fired, a drive signal from the Q-Switch driver 26 is sent to the Q-Switch 24 to deter laser oscillation. Trace "b" shows the laser gain. The gain rises as a result of excitation caused by radiation from the flashlamp 18. Near the peak of the gain, the signal from the Q-Switch drive 26 is removed as indicated on trace "c" at time t1.

A large first output pulse is generated by the laser rod 16, as indicated at t1, in trace "d". The laser gain drops as energy is output as is evidenced in trace "b". The Q-Switch driver 26 signal is restored and the gain rises once again. When the gain has recovered to its near maximum, the Q-Switch drive 26 is again removed and a further (second) large output pulse is produced from the laser 16 at time t2.

A typical flashlamp excited solid state laser such as an Alexandrite laser uses a gain medium typically in the shape of a cylindrical rod, as may be seen in FIG. 1. The flashlamp 18 provides radiation needed to excite the laser rod 16, and the reflective chamber 19 is used to insure that the radiation from the lamp reaches the laser rod. The radiation from the flashlamp excites the gain medium. Spontaneous radiation is thus emitted from the excited gain medium. Some of this radiation is reflected back into the gain medium by a pair of carefully aligned mirrors 23 and 25 that form a resonator. This radiation experiences amplification as it traverses the gain medium. One of the mirrors 25 is partially transmitting thus allowing a useful output from the laser rod 16. Stable laser oscillation begins when the round trip gain experienced by the radiation exactly balances the round trip losses, including the amount of radiation that exits the laser 10 as useful output.

If a large loss is introduced in the laser resonator, the gain needed to achieve laser oscillation will be very large. A large amount of energy can be deposited in the laser rod 16 and a large gain achieved without laser oscillation taking place. If the losses are removed very rapidly while the gain in the medium is very high, the resulting laser will be well above threshold. The radiation in the resonator will grow very rapidly and a giant, short pulse will be developed and a portion of the energy previously deposited in the rod 16 will be its output. This is the process identified hereinabove as "Q-Switching".

The fraction of the energy stored in the rod 16 that is extracted in a Q-Switched pulse depends on a number of factors including how much above threshold the laser is immediately after the losses are removed from the resonator, the energy resident in the rod at that time, and an inherent quantity of the gain medium commonly called the "saturation" fluence. This is the fluence that must be present in the resonator in order to extract a large fraction of the energy stored in the rod 16. The saturated fluence is the ratio of the emitted photon energy divided by the stimulated emission cross-section of the material. For the case of Alexandrite, the stimulated emission cross-section is very small, resulting in a large saturation fluence. As a result, in a common Alexandrite laser under flashlamp excitation, only a small fraction of the energy stored is extracted in the Q-Switch process. A significant fraction remains stored in the rod. If the resonator losses are restored, and the flashlamp excitation is extended past the time where the Q-Switch pulse was extracted, the stored energy in the rod will once again increase. Since a significant amount of energy is already present in the rod, the stored energy will reach a level equal to the level at which the first pulse was extracted with less energy from the flashlamp. That is, a second pulse whose energy is equal to that of the first may be extracted from the rod. The generation of this second pulse will require less additional energy than that of the first one. The process may be continued for additional pulses.

To achieve efficient two pulse operation, the time between the two pulses on trace "d" should not exceed the radiative lifetime of the excited medium. For the case of flashlamp excited Alexandrite, this time "window" is of the order of 100 μs or less. It follows then that a dual pulse Alexandrite laser having a wavelength of about 755 nm and maximum fluence of about 30 J/cm$^2$ at 2.4 mm; about 20 J/cm$^2$ at 3.0 mm; or about 7 J/cm$^2$ at 5 mm can meet the requirements set forth for a dual pulse tattoo or pigmented lesion treatment.

We claim:

1. A method of treating a pigmented lesion or tattoo site on tissue of a human patient in a lasing procedure by the steps of:
    irradiating said lesion by a first single pulse Q-Switched laser beam directed onto said site; and
    irradiating said lesion by a second single pulse Q-Switched laser beam directed onto said site within a time interval of less than about 100 μs alter said first pulse.

2. The method as recited in claim 1 including the step of:
    irradiating said lesion by a further single pulse Q-Switched laser beam directed onto said site within said time interval of less than about 100 μs.

3. The method as recited in claim 1, wherein said first pulse and said second pulse each have a range of pulse duration of about 50 nanoseconds to about 75 nanoseconds.

4. The method as recited in claim 1, wherein said first pulse and said second pulse each have a pulse duration of about 60 nanoseconds.

5. The method as recited in claim 1, wherein said Q-switched laser is comprised of Alexandrite.

6. The method as recited in claim 5, wherein said Alexandrite laser has a wavelength of about 755 nm.

7. The method as recited in claim 5, wherein said Alexandrite laser has a maximum fluence of about 30 J/cm$^2$ at 2.4 mm.

8. The method as recited in claim 5, wherein said Alexandrite laser has a maximum fluence of about 20 J/cm$^2$ at 3.0 mm.

9. The method as recited in claim 5, wherein said Alexandrite laser has a maximum fluence of about 7 J/cm$^2$ at 5.0 mm.

10. A flashlamp excited Alexandrite laser arrangement with a driven laser rod for the treatment of a site of pigmented lesions and/or tattoos, said arrangement including:

an Alexandrite laser;

a Q-Switch driver for effecting a Q-Switching of said Alexandrite laser to output single laser pulses onto said site to be treated wherein at least two single pulses are enabled to be applied to said site within a time window equivalent to about 100 µs, and wherein each of said single laser pulses have a pulse duration in a range of about 50 nanoseconds to about 75 nanoseconds.

11. The flashlamp excited Alexandrite laser as recited in claim 10, wherein each of said single laser pulses have a pulse duration of about 60 nanoseconds.

12. The flashlamp exited Alexandrite laser as recited in claim 10, wherein said laser has a wavelength of about 755 nm.

13. The flashlamp exited Alexandrite laser as recited in claim 12, wherein said laser has a maximum fluence of about 30 $J/cm^2$ at 2.4 mm.

14. The flashlamp exited Alexandrite laser as recited in claim 12, wherein said laser has a maximum fluence of about 20 $J/cm^2$ at 3.0 mm.

15. The flashlamp exited Alexandrite laser as recited in claim 12, wherein said laser has a maximum fluence of about 7 $J/cm^2$ at 5.0 mm.

* * * * *